United States Patent [19]

Florent et al.

[11] B 4,013,515
[45] Mar. 22, 1977

[54] PROCESS FOR THE PREPARATION OF THE ANTIBIOTIC 20.798 R.P.

[75] Inventors: Jean Florent; Jean Lunel; Jacques Renaut, all of Paris, France

[73] Assignee: Rhone-Poulenc S.A., Paris, France

[22] Filed: Nov. 25, 1974

[21] Appl. No.: 527,040

[44] Published under the second Trial Voluntary Protest Program on March 23, 1976 as document No. B 527,040.

[30] Foreign Application Priority Data

Nov. 27, 1973 France .................... 73.42191

[52] U.S. Cl. .................................. 195/80 R
[51] Int. Cl.² ................................. C12B 1/00
[58] Field of Search ........... 195/29, 80 R, 96, 51 R

[56] References Cited
UNITED STATES PATENTS 3,562,112  2/1971  Gibian et al. .................... 195/51 R

FOREIGN PATENTS OR APPLICATIONS 1,322,872  7/1973  United Kingdom ............ 195/80 R

*Primary Examiner*—A. Louis Monacell
*Assistant Examiner*—C. A. Fan
*Attorney, Agent, or Firm*—Stevens, Davis, Miller & Mosher

[57] ABSTRACT

20,798 R.P., which has valuable anti-tumor properties, and acid addition salts thereof are prepared by the microbiological reduction of daunorubicin of the formula:

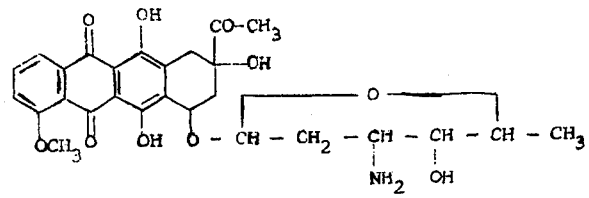

or of an acid addition salt thereof, to convert the grouping —CO—CH$_3$ to —CHOHCH$_3$.

15 Claims, No Drawings

PROCESS FOR THE PREPARATION OF THE ANTIBIOTIC 20.798 R.P.

This invention relates to a new process for the preparation of the antibiotic hereinafter denoted by the number 20,798 R.P., which possesses valuable anti-tumour properties, and has the formula:

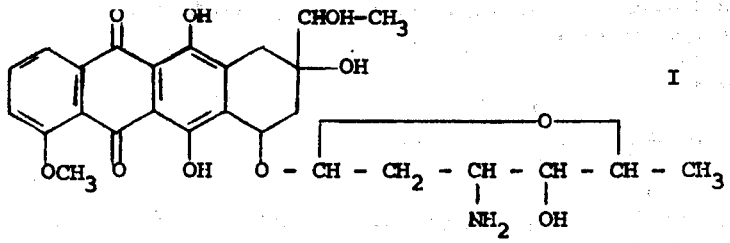

I

The antibiotic 20,798 R.P. and its preparation by cultivation of *Streptomyces coeruleorubidus* (deposited at the United States Department of Agriculture, Northern Regional Research Laboratory, at Peoria, Illinois, United States of America, under the number NRRL 3045) have been described in the specification of our British Patent 1,226,494. The antibiotic 20,798 R.P. is produced in addition to the antibiotic denoted by the number 9,865 R.P., the essential constituent of which is the antibiotic denoted by the number 13,057 R.P., which is called "daunorubicin." Daunorubicin and its preparation have been described in the specification of our British Patent 985598; it has the formula:

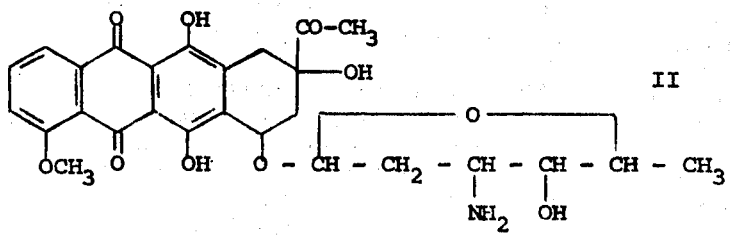

II

The antibiotic 20,798 R.P. can also be prepared by reduction of daunorubicin or one of its acid addition salts by means of an alkali metal borohydride at a temperature of between −20° and +30°C, in accordance with the process which is described in the specification of our British Patent 1,322,872.

It has now been found that the antibiotic 20,798 R.P. can be prepared by microbiological reduction of daunorubicin.

According to the invention the antibiotic 20,798 R.P. or an acid addition salt thereof is produced by microbiological reduction of the grouping -CO-CH$_3$ in daunorubicin or an acid addition salt thereof to the grouping -CHOHCH$_3$.

The reduction is generally carried out in an aqueous medium, employing either cultures of microorganisms which have reached a suitable stage of development, cells isolated from these cultures or enzymatic extracts obtained from these cells.

The microorganisms which can be used in the process of the present invention can belong to the category of streptomycetes or bacteria. Amongst the microorganisms which are particularly suitable are *Streptomyces lavendulae* (ATCC 8664), *Streptomyces roseochromogenes* (ATCC 13400), *Corynebacterium simplex* (ATCC 6946) or *Bacterium cyclooxydans* (ATCC 12673), the best results being obtained from cultures of *Corynebacterium simplex* (ATCC 6946).

The culture of the microorganism which produces the enzyme system capable of reducing daunorubicin to form the antibiotic 20,798 R.P. can be carried out by any of the known aerobic surface culture or submerged culture methods, but the latter are preferred for reasons of convenience. For this purpose, the inoculation and fermentation techniques and the various types of apparatus which are currently used in the fermentation industry may be employed.

The microorganism culture medium must contain assimilable sources of carbon and nitrogen, mineral elements and optionally growth-promoting factors; all these ingredients may be supplied as well-defined products or complex mixtures such as those found in biological products of various origins.

As sources of assimilable carbon, there may be used carbohydrates such as glucose, or other carbohydrate substances such as sugar alcohols or certain organic acids. Certain animal or vegetable oils such as lard oil or soya bean oil may advantageously replace these carbon sources or may be used in admixture with them.

The suitable sources of assimilable nitrogen are extremely varied. They can be very simple chemical substances such as inorganic or organic ammonium salts, urea or certain amino-acids. They can also be complex substances, principally containing nitrogen in a protein form, such as casein, lactalbumin, gluten and their hydrolysis products, soya bean flour, peanut meal, fish meal, peptone, meat extract, yeast extract, distillers' solubles or corn-steep liquor.

Amongst the inorganic substances, some may have a buffering or neutralising effect such as the alkali metal or alkaline earth metal phosphates. Others contribute to the ionic equilibrium necessary for the development of the microorganism, such as alkali metal or alkaline earth metal chlorides and sulphates.

The pH of the culture medium at the start of the culture should be between 6.0 and 7.8, and preferably between 6.5 and 7.5. The optimum temperature for the culture of the microorganism is 29° to 31°C, but satisfactory development is achieved at temperatures between 26° and 37°C. The rate of aeration of the culture medium can vary within quite wide limits. It has, however, been found that aeration rates of 0.3 to 3 liters of air per liter of broth per minute are particularly suitable. In order to obtain a culture which possesses good reducing activity, it is preferably to stir the culture medium, for example by means of a stirrer, the rate of rotation of which may vary between 100 and 250 revolutions/minute. The microorganism culture generally reaches a satisfactory degree of development after a period of 24 to 48 hours.

The reducing activity of the enzyme system thus obtained is of an endocellular nature, which can be demonstrated by the absence of activity of the filtered cultures. Moreover, the reducing activity depends essentially on the amount of cells formed during the culture. With isolated cells, for example after centrifuging the culture medium, the amount of antibiotic 20,798 R.P. formed from daunorubicin is directly related to the concentration of cells in the reaction medium; cell-rich media possess a higher reducing power.

Daunorubicin is reduced to form the antibiotic 20,798 R.P. by bringing an aqueous solution of daunorubicin or one of its acid addition salts into contact with the microorganism culture medium which has reached a sufficient degree of development and has achieved sufficient reducing power, into contact with cells isolated from these cultures or into contact with an enzymatic extract obtained from these cells.

The reduction is generally carried out in a stirred medium, at a temperature of between 23° and 37°C and preferably between 26° and 30°C, and is complete after 1 to 4 days of contact.

The reduction can take place at a pH of between 5 and 10, but a pH of between 7 and 8 is preferred.

The culture medium may be stirred, for example by means of a stirrer, the rate of rotation of which may vary between 100 and 250 revolutions/minute.

The reduction can be carried out either on daunorubicin or one of its pure acid addition salts, or on an impure product, or on the acid filtrate of a culture which has produced daunorubicin. In order to obtain good results, the concentration of daunorubicin in the reducing medium is advantageously between 0.04 and 1 g./l at the start of the reduction.

The antibiotic 20,798 R.P. can be isolated from the reduction medium in accordance with the usual methods for isolating this antibiotic. For example, 20,798 R.P. can be extracted from the culture medium at a pH of about 9 by means of an organic solvent such as chloroform, methylene chloride, n-butanol or a mixture of these solvents.

The antibiotic 20,798 R.P. can be isolated from the organic extracts, after successive washing and extraction processes, by precipitation after concentrating the extracts to a small volume, or by adding a diluent in which the antibiotic 20,798 R.P. is insoluble, such as hexane, after optionally converting the antibiotic into an addition salt with an acid, such as the hydrochloride.

The antibiotic 20,798 R.P. can optionally be purified by conventional purification methods such as crystallisation or chromatography.

The following Examples illustrate the invention. In the following:

a. the coloured extracts are measured by spectrophotometry at 480 nm relative to a standard solution of daunorubicin in the same solvent,
b. the antibiotic 20,798 R.P. is identified by chromatography on a thin layer of silica gel, comparing the Rf values of the products obtained with that of daunorubicin or the antibiotic 20,798 R.P. in the same solvent system, and
c. the production of the antibiotic 20,798 R.P. is assessed from thin layer chromatograms, either by comparing the intensities of the corresponding spots of the extract and that of the pure antibiotic 20,798 R.P. taken as the reference, or by comparing the surface areas of the peaks recorded on a "Chromosan" plate scanner, or finally by colorimetrically determining the antibiotic 20,798 R.P. eluted from the chromatographic support at the spot of the desired product.

EXAMPLE 1

A culture medium A is prepared, the composition of which is as follows:

| | |
|---|---|
| brewer's yeast autolysate powder, "yeast amine" | 5 g. |
| monopotassium phospate | 1 g. |
| dipotassium phosphate | 1 g. |
| distilled water | 900 cc. |

The pH is adjusted to 6.9 with 1N sodium hydroxide solution, and the medium is sterilised at 122°C for 20 minutes. After cooling, a sterile solution of glucose of concentration 50 g./l (100 cc.) is added.

A 300 cc. culture flask containing this medium (50 cc.), the pH of which is 6.9, is inoculated with an inoculum culture of the strain *Corynebacterium simplex* (ATCC 6946) (2.5 cc.). The culture is developed for 24 hours on a shaking table with agitation using a motor rotating at 220 revolutions/minute in a chamber at 30°C. An aqueous solution of daunorubicin hydrochloride of concentration 10 mg./cc. (1 cc.) is then added to the well developed culture, the pH of which is 7.45. The reduction step is continued for 24 hours under the conditions of shaking and the temperature conditions employed for the development of the culture.

When the reduction is complete, the whole culture, the pH of which is 8.4, is treated with a borate buffer (25 cc.) to adjust the pH to 9, and is then extracted with a mixture of methylene chloride and normal butanol (80-20 by volume) (2 × 50 cc.). The organic extracts are dried over anhydrous sodium sulphate.

The extraction yield (90 percent) is determined by measuring the absorption at 480 nm using a spectrophotometer and comparing it with that of daunorubicin under the same conditions.

The production of 20,798 R.P. is assessed by chromatographing the organic extracts on a thin layer of silica gel. The volumes of extracts deposited correspond to amounts of coloured products, measured by spectrophotometric determination, of between 1 and 10 μg. The plates are developed using a mixture of methylene chloride, formic acid and methanol (80-17-3 by volume) in order to achieve good separation between daunorubicin and the antibiotic 20,798 R.P., and the Rf values of the products obtained are compared with those of the reference products chromatographed under the same conditions. Quantitative evaluation of the production of 20,798 R.P. shows that the *Corynebacterium simplex* (ATCC 6946) culture reduces daunorubicin to form the antibiotic 20,798 R.P. in a yield of 73 percent relative to the daunorubicin employed.

EXAMPLE 2 a. Development of the culture and reduction

The production culture is carried out in a 800 liter fermenter, into which the following substances are introduced:

| brewer's yeast autolysate powder, "yeast amine" | 2.50 kg. |
| --- | --- |
| monopotassium phosphate | 0.50 kg. |
| dipotassium phosphate | 0.50 kg. |
| tap water, sufficient to make up to | 460 liters. |

The pH is adjusted to 6.90 with 10N sodium hydroxide solution (225 cc.) and the medium is sterilised by bubbling steam at 122°C through it for 40 minutes. After cooling, the volume of the broth is 494 liters because of the steam condensed during sterilisation; it is made up to 500 liters by adding a sterile aqueous solution (6 liters) containing glucose monohydrate (2.5 kg.). The pH of the medium is 6.90. The medium is then inoculated using an inoculum culture (500 cc.) of the strain *Corynebacterium simplex* (ATCC 6946). The culture is developed at 30°C, with stirring using a motor rotating at 160 revolutions/minute and aeration with sterile air (18 m.³/hour). After 48 hours, the culture is suitable for effecting the biochemical conversion of daunorubicin to the antibiotic 20,798 R.P.

An aqueous solution (4 liters) containing daunorubicin hydrochloride (108 g.) is introduced into the culture.

Incubation is continued for 24 hours at 30°C, with stirring and aeration with sterile air (15 m.³/hour). Daunorubicin is reduced to the antibiotic 20,798 R.P. in a yield of approximately 85 percent.

b. Extraction

A 5N sodium hydroxide solution (55 cc.) is added to the must obtained above (480 liters) to adjust the pH to 9. The active principle is extracted in countercurrent by means of a mixture of n-butanol and water (6-4 by volume) on two centrifuges. The extract, the volume of which is 305 liters, is concentrated under reduced pressure (5 to 10 mm Hg) at 40°C until its volume is 20 liters.

The concentrated extract is washed with water (10 liters) which has been rendered alkaline until its pH is 9. As some of the antibiotic 20,798 R.P. is carried away in the wash water, the latter is extracted with methylene chloride (2 × 10 liters). n-Butanol (10 liters) is added to the methylene chloride phase after it has been concentrated to a volume of 10 liters. After concentration to 5 liters the concentrate is combined with the first butanol extract and the combined solution is concentrated to a volume of 5 liters. n-Butanol (50 cc.) containing 10 percent by volume of 10N hydrochloric acid is then added, with stirring, and the mixture is concentrated under reduced pressure (5 to 10 mm Hg) at 40°C until its volume is 3 liters.

The antibiotic 20,798 R.P., in the form of the hydrochloride, is precipitated when the solution obtained is added slowly to hexane (30 liters), whilst stirring. The precipitate is filtered off, washed and dried. The hydrochloride of the antibiotic 20,798 R.P. (105 g.) is thus obtained.

c. Purification

The hydrochloride of 20,798 R.P. (159 g.), obtained as indicated above, is dissolved in methanol (795 cc.). The product which crystallises is filtered off, washed and then dried. The hydrochloride of 20,798 R.P. in crystalline form (111 g.), the purity of which is 80 percent, is thus obtained.

The product thus obtained (111 g.) is dissolved in water (666 cc.). The solution is filtered through a sterilising membrane (pore diameter: 0.22 $\mu$). The hydrochloride of the antibiotic 20,798 R.P. crystallises when acetone (6.6 liters) is added slowly. The crystals are filtered off, washed and dried. The hydrochloride of the antibiotic 20,798 R.P. in pure form (93.1 g.) is thus obtained.

EXAMPLE 3

A culture medium A, as described in Example 1, is prepared and distributed in 300 cc. culture flasks. The sterilised flasks are inoculated with an inoculum culture of the strain *Corynebacterium simplex* (ATCC 6946) and are incubated at 30°C on a shaking table with agitation using a motor rotating at 220 revolutions/minute for 24 to 48 hours.

Daunorubicin is then added to the whole culture, the daunorubicin being in the form of:

a. an aqueous solution of the pure product of concentration 10 mg./cc., added at the rate of 1 or 2.5 cc. per flask (to give a concentration of 0.2 or 0.5 g./l), or b. an aqueous solution of a crude product containing 47 percent of 13,057 R.P., the concentration of the aqueous solution being 10 mg./cc., added at the rate of 1 or 2.5 cc. per flask (to give a concentration of 0.095 or 0.24 g. of daunorubicin/liter).

The flasks are then incubated for at least 24 hours under the conditions described in Example 1 and are treated in the same way. The results are given in the following Table:

| | Yield of antibiotic 20,798 R.P. obtained (in %) | | | |
| --- | --- | --- | --- | --- |
| | Amount of daunorubicin added in g./l | | | |
| Reducing medium: | Pure product | | Crude product | |
| | 0.2 | 0.5 | 0.095 | 0.24 |
| 24 hour whole culture | 73 | 42 | 87 | 60 |
| 30 hour whole culture | 74 | 53 | 78 | 64 |
| 48 hour whole culture | 90 | 70 | 89 | 58 |

EXAMPLE 4

Cultures of the strain *Corynebacterium simplex* (ATCC 6946) are prepared under the conditions described in Example 1. Using these 24 or 30 hour cultures, the daunorubicin present in the oxalic acid filtrate of a culture of the strain *Streptomyces coeruleorubidus* (NRRL 3045), which produces daunorubidin, is reduced. After this filtrate has been freed from oxalic acid by treatment with calcium carbonate, it contains daunorubicin (90 mg./l) and its pH is 7.0. It is used at the rate of 1 volume per 1 volume of whole culture of *Corynebacterium simplex* (ATCC 6946). The flasks containing this reaction mixture (50 cc.) (0.045 g. of daunorubicin/liter) are then incubated for at least 24 hours under the conditions described in Example 1 and are treated in the same way.

24 and 30 hour cultures of *Corynebacterium simplex* (ATCC 6946) reduce daunorubicin to form the antibiotic 20,798 R.P., in yields of 84 and 100 percent respectively, relative to the daunorubicin employed.

EXAMPLE 5

Cultures of the strain *Corynebacterium simplex* (ATCC 6946) are prepared under the conditions described in Example 1 and the cells produced by these cultures after they have been developed for 30 hours are collected by centrifuging. The reduction of daunorubicin (of different degrees of purity) to form the antibiotic 20,798 R.P. is carried out, using these cells suspended in:

a. 0.15 M phosphate buffer (50 cc.) at pH 8.0, receiving an aqueous solution of pure daunorubicin (2.5 cc; concentration 10 mg./cc.) to give a concentration of 0.5 g./l., b. a 0.15 M phosphate buffer (50 cc.) at pH 8.0, receiving an aqueous solution of daunorubicin in the form of a crude product containing 47 percent of pure daunorubicin (2.5 cc; concentration of crude product 10 mg./cc.) to give a concentration of 0.24 g./l. in terms of pure daunorubicin, and c. the oxalic acid filtrate (50 cc.) of a culture of the strain *Streptomyces coeruleorubidus* (NRRL 3045) prepared as described in Example 4. Under these conditions, the reaction medium contains 0.090 g. of pure daunorubicin/liter.

The flasks are then incubated for 24 hours under the conditions described in Example 1 and are treated in the same way. The yields of the antibiotic 20,798 R.P. are as follows: 85 percent from 0.5 g./l of daunorubicin used in the pure state, 77 percent from 0.24 g./l of daunorubicin used in the form of a crude product containing 47 percent of daunorubicin, and 91 percent from 0.090 g./l of daunorubicin present in the filtrate of a culture of *Streptomyces coeruleorubidus*.

EXAMPLE 6

Inoculum cultures of *Bacterium cyclooxydans* (ATCC 12,673), of *Streptomyces roseochromogenes* (ATCC 13,400) and of *Streptomyces lavendulae* (ATCC 8664) are used to inoculate media A, B and C (defined in the Table below) distributed in 300 cc. culture flasks (50 cc. per flask). The cultures are developed at 26 or 30°C on shaking tables with agitation using a motor rotating at 220 revolutions/minute until a large amount of biological material is obtained. An aqueous solution (1 or 2.5 cc.) of daunorubicin of concentration 10 mg./cc. (to give 0.2 or 0.5 g./l) is then added to each flask and reduction is carried out by keeping these flasks, for 1 to 3 days after the addition, under the same conditions of temperature and shaking as those used to develop the culture. The cultures are treated and analysed under the conditions described above. The results are given in the following Table:

| Micro-organism used | Development medium (composition in g./l) | | Conditions used for the development and reduction (temperature; shaking) | Age of the cultures at the time of adding daunorubicin | Antibiotic 20,798 RP obtained in % | |
|---|---|---|---|---|---|---|
| | | | | | Daunorubicin added in g./l | |
| | | | | | 0.2 | 0.5 |
| B. cyclo-oxydans (ATCC 12673) | Medium A: Yeast amine glucose monopotassium phosphate dipotassium phosphate | 5 5 1 1 | 30°C; 220 revolutions/minute | 24 hours 30 hours | 72 72 | — 19 |
| S. roseo-chromo-genes (ATCC 13400) | Medium B: Soya flour glucose soya oil dipotassium phosphate calcium carbonate | 20 4.1 5.0 1.0 2.5 | 26°C; 220 revolutions/minute | 30 hours 54 hours | 35 48 | 52 32 |
| S. laven-dulae (ATCC 8664) | Medium C: Soya flour glucose soya oil monopotassium phosphate calcium carbonate | 30 50 5 1 2.5 | 26°C; 220 revolutions/minute | 30 hours 54 hours | 29 30 | 31 21 |

In the foregoing Examples the abbreviation ATCC stands for American Type Culture Collection.

Preferably acid addition salts employed in the process of the present invention are non-toxic acid addition salts, i.e., salts containing anions which are relatively innocuous to the animal organism in therapeutic doses of the salts, such as inter alia hydrochlorides, sulphates, nitrates, acetates and propionates.

We claim:

1. Process for the preparation of the antibiotic 20,798 RP of the formula:

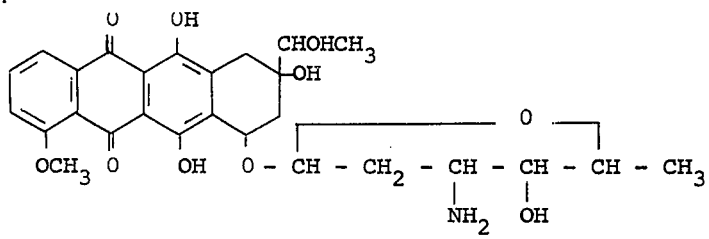

or an acid addition salt thereof, which comprises the microbiological reduction of daunorubicin of the formula:

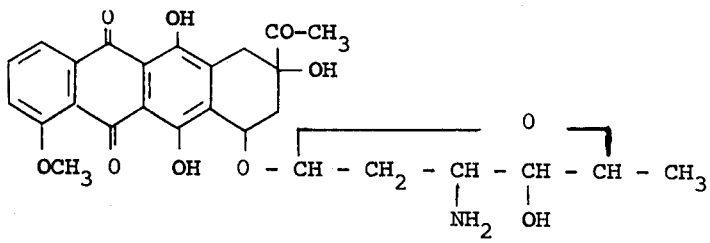

or of an acid addition salt thereof using *Streptomyces lavendulae* (ATCC 8664), *Streptomyces roseochromogenes* (ATCC 13400). *Corynebacterium simplex* (ATCC 6946) or *Bacterium cyclooxydans* (ATCC 12673), to convert the grouping –CO—CH$_3$ to —CHOHCH$_3$.

2. Process according to claim 1 in which an aqueous solution of daunorubicin or a salt thereof is contacted with a culture medium containing a said micro-organism.

3. Process according to claim 1 in which an aqueous solution of daunorubicin or a salt thereof is contacted with cells isolated from a culture of a said micro-organism.

4. Process according to claim 1 in which an aqueous solution of daunorubicin or a salt thereof is contacted with an enzymatic extract isolated from cells of a said micro-organism.

5. Process according to claim 1 in which the microorganism is *Corynebacterium simplex* (ATCC 6946).

6. Process according to claim 1 in which the reduction is carried out at between 23° and 37°C in a stirred medium.

7. Process according to claim 6 in which the reduction is carried out at between 26° and 30°C.

8. Process according to claim 1 in which the reduction is effected at a pH between 5 and 10.

9. Process according to claim 8 in which the pH is between 7 and 8.

10. Process according to claim 1 in which the reduction is carried out in a medium stirred with a stirrer rotating at between 100 and 250 revolutions/minute.

11. Process according to claim 1 in which the concentration of daunorubicin at the start of the reduction is between 0.04 and 1 g./l.

12. Process according to claim 1 in which 20,798 R.P. is extracted from the culture medium by means of chloroform, methylene chloride, n-butanol or a mixture thereof.

13. Process according to claim 10 in which 20,798 R.P. is extracted from the culture medium at about pH 9.

14. Process according to claim 10 in which 20,798 R.P. is isolated from its organic solution by concentrating the solution under reduced pressure and precipitating the antibiotic from the concentrate by addition of a non-solvent or poor solvent for 20,798 R.P.

15. Process according to claim 12 in which 20,798 R.P. is precipitated from the concentrated solution by the addition of hexane.

* * * * *